(12) United States Patent
He et al.

(10) Patent No.: US 7,623,238 B1
(45) Date of Patent: Nov. 24, 2009

(54) SYSTEM FOR AND METHOD OF REDUCING CHANGE CAUSED BY MOTOR VIBRATIONS IN ELLIPSOMETERS, POLARIMETERS OR THE LIKE

(75) Inventors: Ping He, Lincoln, NE (US); Martin M. Liphardt, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 328 days.

(21) Appl. No.: 11/809,725

(22) Filed: Jun. 2, 2007

Related U.S. Application Data

(60) Provisional application No. 60/811,391, filed on Jun. 7, 2006.

(51) Int. Cl.
G01J 4/00 (2006.01)
(52) U.S. Cl. ...................... 356/369; 356/364
(58) Field of Classification Search ................. 356/364, 356/369
See application file for complete search history.

(56) References Cited

U.S. PATENT DOCUMENTS

| | | | | |
|---|---|---|---|---|
| 5,750,272 | A | 5/1998 | Jardine | 428/686 |
| 6,690,473 | B1 * | 2/2004 | Stanke et al. | 356/601 |
| 6,819,426 | B2 | 11/2004 | Sezginer et al. | 356/401 |
| 6,829,054 | B2 * | 12/2004 | Stanke et al. | 356/601 |
| 6,935,201 | B2 | 8/2005 | Abraham et al. | 73/865.8 |
| 7,042,569 | B2 | 5/2006 | Sezginer | 356/401 |
| 7,061,615 | B1 | 6/2006 | Lowe-Webb | 356/401 |
| 7,173,699 | B2 | 2/2007 | Xu et al. | 356/369 |
| 7,196,328 | B1 | 3/2007 | Kley | 250/306 |
| 7,270,472 | B2 * | 9/2007 | Carreras | 366/111 |
| 2002/0158193 | A1 | 10/2002 | Sezginer et al. | |
| 2004/0050189 | A1 | 3/2004 | Abraham et al. | |
| 2004/0080757 | A1 * | 4/2004 | Stanke et al. | 356/601 |
| 2005/0018190 | A1 | 1/2005 | Sezginer et al. | |
| 2006/0187743 | A1 * | 8/2006 | Carreras | 366/111 |

* cited by examiner

*Primary Examiner*—Roy Punnoose
(74) *Attorney, Agent, or Firm*—James D. Welch

(57) ABSTRACT

A system and method which reduces change in locus of a beam of electromagnetic radiation which otherwise result from vibrations caused by operation of a motor which controls the rotation of an element which affects the beam.

6 Claims, 4 Drawing Sheets

SYSTEM FOR AND METHOD OF REDUCING CHANGE CAUSED BY MOTOR VIBRATIONS IN ELLIPSOMETERS, POLARIMETERS OR THE LIKE

This Application Claims Benefit of Provisional Application 60/811,391 Filed Jun. 7, 2006.

TECHNICAL FIELD

The present invention relates to systems which direct beams of electromagnetic radiation onto samples such as ellipsometer, polarimeter or the like systems, which contain at least one motor driven rotating, or rotatable element. More particularly the present invention is a system and method which reduces change in beam locus as a result of vibrations caused by operation of said motor.

BACKGROUND

It is known to direct a beam of electromagnetic radiation at a sample, optionally via a focusing means, such that said beam is focused onto a very small spot on said sample. It is further known to monitor a sequence of beam polarization states which are imposed on said beam and which are affected by interaction with said sample. Often said polarization states are mediated by application of a motor to effect continuous rotation, or stepped rotation of an element such as a polarizer, compensator or analyzer.

A problem which develops in very precise measurements is that vibrations caused by operation of said motor can affect the location on said sample where the beam impinges by altering the beam locus. In said very precise work the specific location on a sample where the focused beam impinges can affect how the polarization state of the beam is changed by interaction with said sample, and if the impingement position changes even a very small amount, the measurement results will not accurately represent the location it is intended to investigate. Further, undamped vibrations can have an effect on other components in a system.

A computer search for relevant patents has provided:
U.S. Pat. No. 6,935,201 to Abraham et al.;
U.S. Pat. No. 5,750,272 to Jardine;
U.S. Pat. No. 6,819,426 to Sezginer et al.;
U.S. Pat. No. 6,690,473 to Stanke et al.;
U.S. Pat. No. 6,829,054 to Stanke et al.;
U.S. Pat. No. 7,042,569 to Sezginer;
U.S. Pat. No. 7,173,699 to Xu et al.;
U.S. Pat. No. 7,196,328 to Kley;
U.S. Pat. No. 7,061,615 to Lowe-Webb;

In addition Published Patent Applications:
No. US 2002/0158193 A1 by Sezginer et al.;
No. US 2004/0050189 A1 by Abraham et al.;
No. US 2004/0080757 A1 by Stanke et al.;
No. 2005/0018190 A1, by Sezginer et al.

Need remains for a simple to apply system and method for damping vibrations in ellipsometer or the like systems.

DISCLOSURE OF THE INVENTION

The present invention is found in the practice of securing the motor which is used to cause continuous rotation, or stepped rotation of an element such as a polarizer, compensator or analyzer or the like, (eg. means for imposing or monitoring polarization states of a beam of electromagnetic radiation), in an ellipsometer or polarimeter or the like, via means for damping vibrations caused thereby. Other elements of the system which direct the beam to a sample being investigated, (eg. a focusing means etc.), are then not subjected to position and/or orientation changes because of vibrations caused by the motor operation being transmitted thereto. The end result is that the beam locus is not affected by the vibrations as much as they would be if the damping means were not present.

The present invention system can be described as comprising a motor driven component and a means for providing a beam of electromagnetic radiation to a specific small location on a sample along a locus, said system further comprising a means for damping vibrations caused by the operation of said motor such that vibrations do not cause displacement of the beam locus. Various means for damping vibrations caused by the operation of said motor comprise:

- making a system element to which the motor is secured relatively more massive than is required to simply secure its position;
- applying a separate securing means which secures said motor to an adjacent stationary support;
- securing the motor by a support which is separate from that which secures other components;
- securing the motor to a support element via damping means, (eg. spring providing material or the like).

Another recitation of a present invention system for maintaining the locus of a beam of electromagnetic radiation, provides that said system comprise a source means for providing a beam of electromagnetic radiation and a motor driven component, said system further comprising a means for damping vibrations caused by the operation of said motor such that vibrations do not cause displacement of the beam locus. Said system is characterized by further comprising a polarizer, an analyzer, a detector and mounting arms, with said source means and polarizer being mounted to one said mounting arm and said analyzer and detector being mounted to another of said mounting arms. In use said motor is applied to drive a beam polarization state changing element, (eg. polarizer, analyzer, compensator). The system is characterized by the presence of a means for damping vibrations, the purpose thereof being to damp vibrations produced by the operation of said motor so that change in the locus of the beam is reduced. This has the effect of maintaining the location on a sample at which said electromagnetic beam impinges thereupon.

A present invention system can then comprise:
a motor driven component which is mounted to a stationary support; and
a means for providing a beam of electromagnetic radiation to a small location on a sample;

said system further comprising a means for damping vibrations caused by the operation of said motor such that vibrations cause less change in beam locus than would otherwise result.

Said present invention system can further comprises means for imposing polarization states on said beam of electromagnetic radiation which are changed via operation of said motor.

Said system can further comprise means for damping vibrations caused by the operation of said motor comprising securing means which secures said motor to a stationary support separate from that to which said motor is mounted.

Said system can further comprise means for damping vibrations caused by the operation of said motor comprising said motor being secured to said stationary support vibration absorbing via spring material damping means.

Said system can further comprise means for damping vibrations caused by the operation of said motor in the form of a securing means which secures said motor to said stationary support, said stationary support being more massive than necessary to support the motor.

Said system can further comprise means for damping vibrations caused by the operation of said motor comprising a securing means which secures said motor to a stationary support, said stationary support having an additional stationary support secured thereto to increase vibration damping capacity.

A present invention method of maintaining the location on a sample at which a beam of electromagnetic radiation impinges thereupon comprising the steps of:
 a) providing a system comprising a motor driven component and a means for providing a beam of electromagnetic radiation to a small specific location on a sample, said system further comprising a means for damping vibrations caused by the operation of said motor such that vibrations do not cause displacement of the beam locus;
 b) causing said means for damping vibrations caused by the operation of said motor to be functionally secured to said motor;
 c) causing said electromagnetic beam to impinge on said sample while causing said motor to operate, and while detecting electromagnetic radiation emerging from said sample with a data detector;

to the end that vibrations produced by the operation of said motor cause less change in the locus of said electromagnetic beam than would be the case if said means for damping vibrations caused by the operation of said motor were not functionally secured thereto.

Said motor can cause continuous or step-wise rotation of a polarization causing, modifying or monitoring element. For instance, a compensator might be caused to continuously rotate while data is obtained, while a polarizer and/or analyzer might be caused to stepwise rotate. Thus, the present invention includes applying multiple vibration damping means to a corresponding multiple of polarization causing, modifying or monitoring elements, which can be present in a system such as an ellipsometer or polarimeter.

Another present invention method of maintaining the location on a sample at which a beam of electromagnetic radiation impinges thereupon comprising the steps of:
 a) providing a system comprising a motor driven component and a means for providing a beam of electromagnetic radiation provided by a source thereof to a small location on a sample, said system further comprising a means for damping vibrations caused by the operation of said motor such that vibrations do not cause displacement of the beam on said sample, said system further comprising a polarizer and analyzer and detector and mounting arms; said source and polarizer and optionally a focusing means being mounted to one said arm; and optionally another focusing means, an analyzer and a detector being mounted to another of said arms, with said motor driven component being mounted to one or the other of said arms;
 b) if not accomplished in step a causing said means for damping vibrations caused by the operation of said motor to be functionally applied to said motor;
 c) causing said electromagnetic beam to impinge on said sample while causing said motor to operate, and while detecting electromagnetic radiation emerging from said sample with a data detector;

to the end that vibrations produced by the operation of said motor cause less change in the location of beam locus than would be the case if said means for damping vibrations caused by the operation of said motor were not functionally secured thereto.

Said method can further comprise the step of disconnecting attachment of said motor driven component to its mounting to one or the other of said arms.

It is further noted that methodology of the present invention can be characterized by at least one selection from the group consisting of:
 storing at least some data provided by said data detector in machine readable media;
 analyzing at least some of the data provided by said data detector and storing at least some of the results of said analysis in machine readable media;
 displaying at least some data provided by said data detector by electronic and/or non-electronic means;
 analyzing at least some of the data provided by said data detector and displaying at least some of the results of said analysis by electronic and/or non-electronic means;
 causing at least some data provided by said data detector to produce a signal which is applied to provide a concrete and tangible result;
 analyzing at least some of the data provided by said data detector and causing at least some thereof to produce a signal which is applied to provide a concrete and tangible result.

The present invention will be better understood by reference to the Detailed description Section of this Specification, with reference to the Drawings.

DETAILED DESCRIPTION

Figure 1:
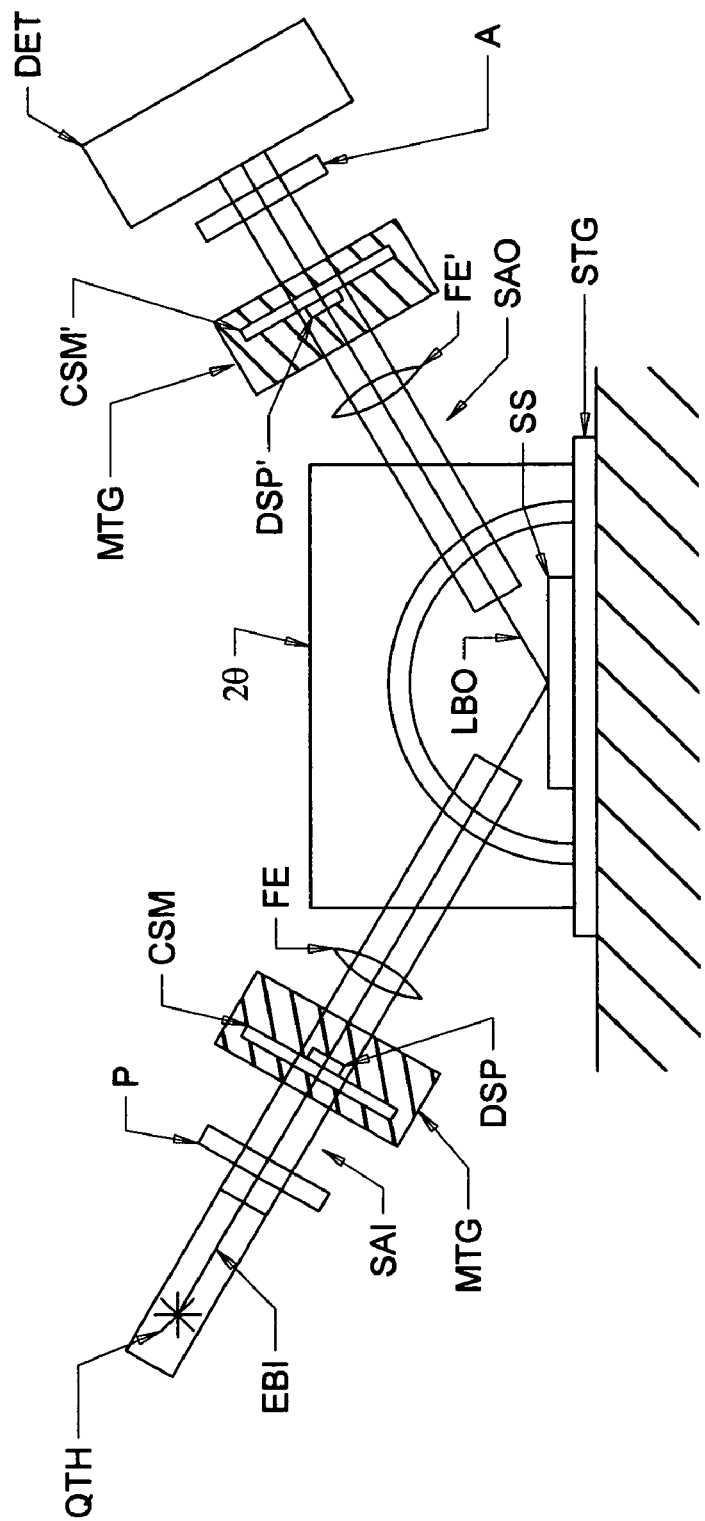
FIG. 1 demonstrates, in side elevation, an ellipsometer system.

FIG. 1 demonstrates that an ellipsometer system can comprise a Source of a beam of electromagnetic radiation (QTH), a Polarizer (P), a Continuously Rotating or Stepped Motor (DSM) in combination with a Compensator (CSM), a Focusing Means (FE), a Sample (SS) on a Stage (STG), a Collimating Focusing Means (FE'), optionally a second Stepped Motor (DSP') in combination with a Compensator (CSM'), an Analyzer (A) and a Detector (DET). Physical systems typically mount all said elements to arms Arms (SAI) (SAO) which project at some oblique angles as shown in FIG. 1. Such mounting allows for vibrations caused by operation of a Motor (DSM) to propagate to the Focusing Elements (FE) and/or (FE'), and motion thereof leads to changed location of the electromagnetic beam on said Sample (S).

The present invention can be demonstrated by the provision of at least one additional mounting element, (see the elements identified as (MTG) and (MTG'), in FIG. 1), which damp vibrations caused by operation of one or more of said Motors (DSM) (DSM') which are caused to operate, and which can be firmly secured to some external support, thereby reducing the need to be attached to the same supports, (i.e. (SAI) (SAO), as are other elements, (eg. (QTH) (FE) (FE') (P) (A) and (DET)).

A method of the present invention begins by recognizing that the components of an ellipsometer or polarimeter or the like as shown in FIG. 1. are conventionally mounted to rigid arms (A1) (A2). For instance (QTH) (P) (DSP/CSM) and (FE) are mounted to one rigid arm (SA1), and (FE') (DSP'/CSM') (A) and (DET) are mounted to another rigid arm (SAO). Said rigid arms (SA1) and (SAO) are projected at an Angle-of-Incidence and Angle-of-Reflection, respectively. In use the system is set-up as shown and adjustments performed to calibrate it. Such is well known procedure. The present invention method does not change that, but adds an additional step. During or after the system is set-up and calibrated, vibration damping means (MTG) and (MTG') are secured to (DSP/CSM) and/or (DSP'/CSM') and/or (DSP/CSM) respectively, (note that only one of said (DSP/CSM) and/or (DSP'/CSM') might be present). Said vibration damping means (MTG) and (MTG') can in turn be secured to some rigid vertically oriented support, and connection between the arms of the ellipsometer, polarimeter or the like which secured them during set-up and calibration, along with (QTH) (P) and (FE), and (FE') (A) and (DET), can even be disconnected. This isolates all vibrations caused by (DSP/CSM) and or (DSP'/CSM') from affecting (QTH) (P) and (FE), and (FE') (A) and (DET) which remain attached to said arms (SAI) (SAO). (Note, the Mountings (MTG) (MTG') in FIG. 1 can be considered to be the Mounting (MTG) shown in FIG. 2, only rotated to project into the page to contact with a rigid support, rather than project downward to a rigid support.

Figure 2A:
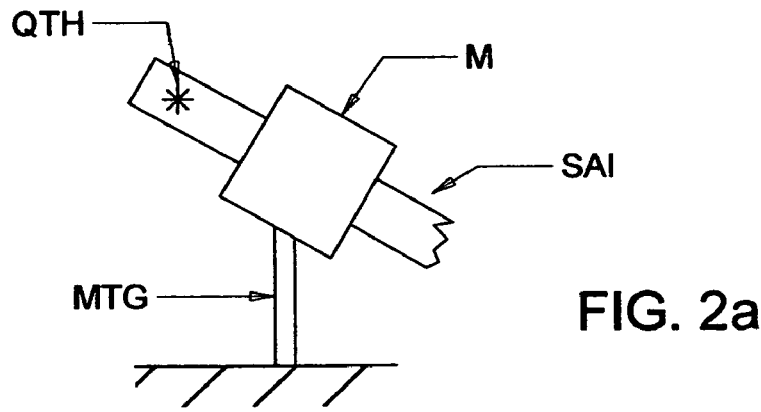
FIG. 2a demonstrates, in side elevation, a partial view of a physical realization of the present invention system support arm with a motor containing element affixed thereto.

FIG. 2a demonstrates a partial view of a physical realization of the present invention system support arm (SAI) with a motor containing element (M) affixed thereto. Note that the directly identified Motor (M), (which corresponds to (CSM) or (CSM') in FIG. 1, is attached to a Mounting (MTG) which is supported from below. This is in contrast to the Mountings (MTG) shown in FIG. 1 which project into the plane of the paper and are attached to a vertical support.

Figure 2C:
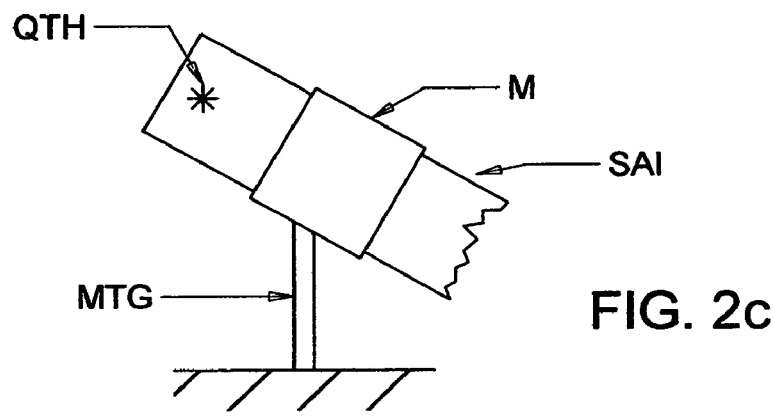
FIG. 2c demonstrates, in side elevation, a partial view of a physical realization of a more massive present invention system support arm, as compared to that shown in FIG. 2a, with a motor containing element affixed thereto.
Figure 2D:
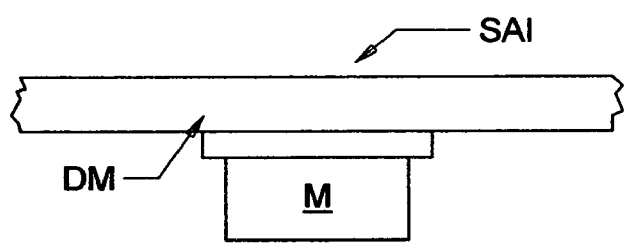
FIG. 2d demonstrates, from the top, a partial view of a physical realization of the present invention system support arm with a motor containing element affixed thereto via vibration damping elements.
Figure 2E:
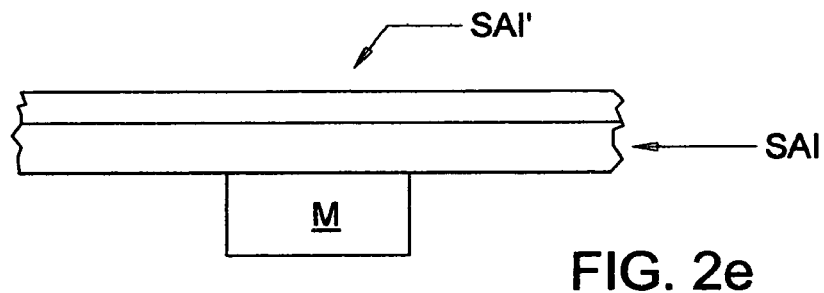
FIG. 2e demonstrates, from the top, a partial view of a physical realization of the present invention system support arm with a motor containing element affixed thereto, said support arm having an additional support element affixed thereto.
Figure 2B:
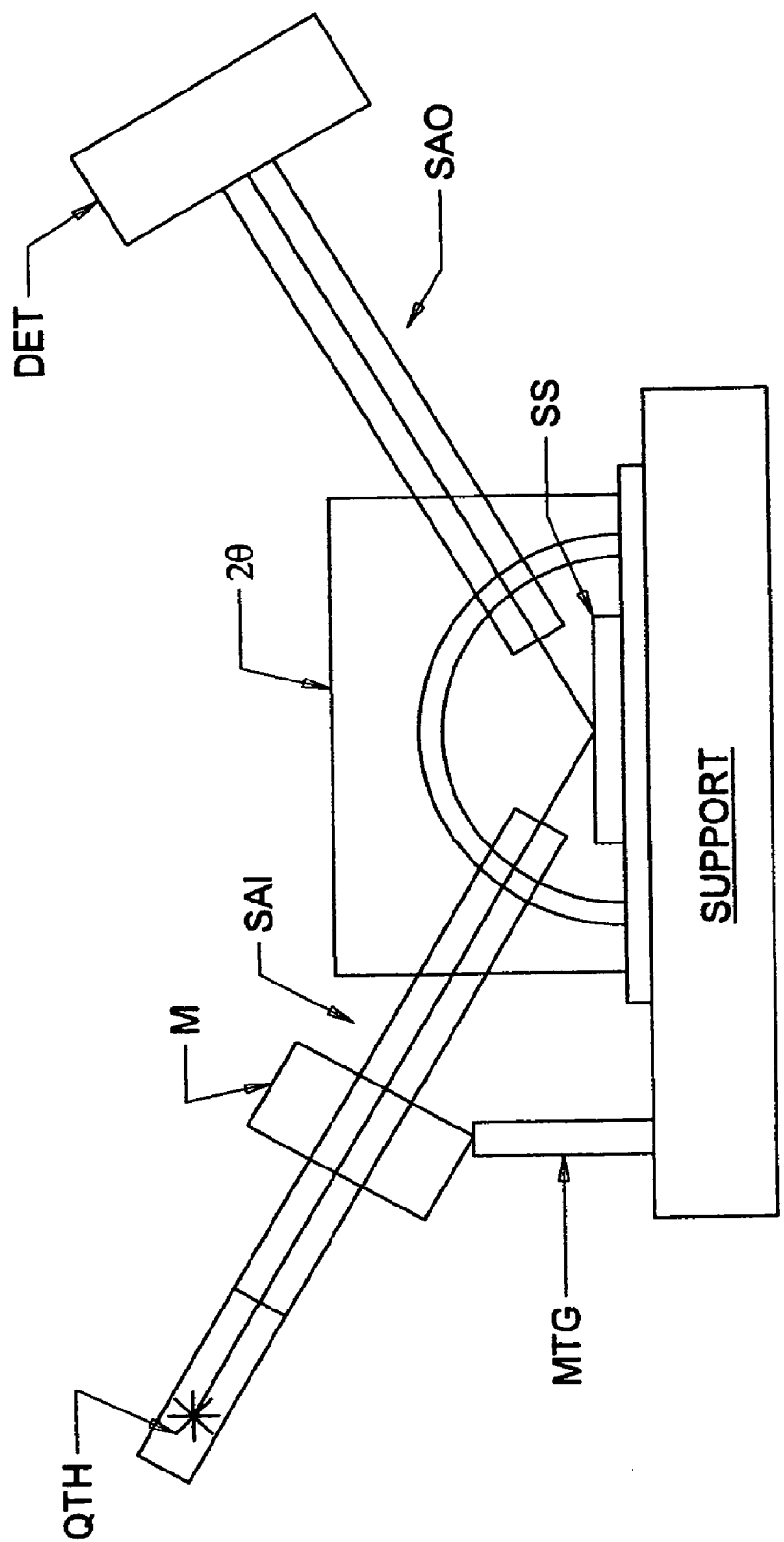
FIG. 2b demonstrates, in side elevation, a physical realization of the present invention system support arm with a motor containing element affixed thereto, with an additional stationary support separate from that to which said motor is mounted present to provide vibration damping.

FIG. 2b shows a partial view of a physical realization of the present invention system support arm (SAI) with a motor containing element affixed thereto, with an additional stationary support (MTG) separate from that to which said motor containing element (M) is mounted present to provide vibration damping. Note that the vibration damping means stationary support (MTG) is solidly connected between a base Support and the element containing the motor (M). It is noted that use of this sort of stationary support is not known in the ellipsometers and polarimeters area because it complicates changing the angle-of-incidence at which a beam approaches a sample, however, where vibrations are a concern the additional difficulty involved in applying it can be justified. Known prior art teach away from providing such vibration damping means stationary support (MTG), in favor of teaching convenience of changing beam angle-of-incidence in use.

FIG. 2b can also be interpreted to demonstrate that the motor containing element (M) can be supported by the vibration damping means stationary support (MTG) alone and not be connected to the support arm (SAI) at all. That is, FIG. 2b demonstrates that the motor containing element (M) can be, or not, secured to the system support arm (SAI), but that a separate vibration damping means support (SA') is present to support the motor containing element (M).

FIG. 2b also indicates that an angle-of-incidence setting means, (eg. a 2 means which sets input and output angles-of-incidence to be equal), is typically applied to orient the support arms (SAI) and (SAO) without the use of any vibration damping means stationary support (MTG).

FIG. 2c demonstrates a partial view of a physical realization of a more massive present invention system support arm (SAI), as compared to that shown in FIG. 2a, with a motor containing element (M) affixed thereto. The additional mass serves to surpress vibrations.

FIG. 2d demonstrates, from a top view, a partial view of a physical realization of the present invention system support arm (SAI) with a motor containing element (M) affixed thereto via vibration damping spring elements (DM). The damping means, (eg. spring providing material), serves to surpress vibrations.

FIG. 2e demonstrates, from a top view, a partial view of a physical realization of the present invention system support arm (SAI) with a motor containing element (M) affixed thereto, said support arm having an additional support element (SA') affixed thereto. The additional rigidity provided by (SAI') serves to surpress vibrations.

Figure 3:
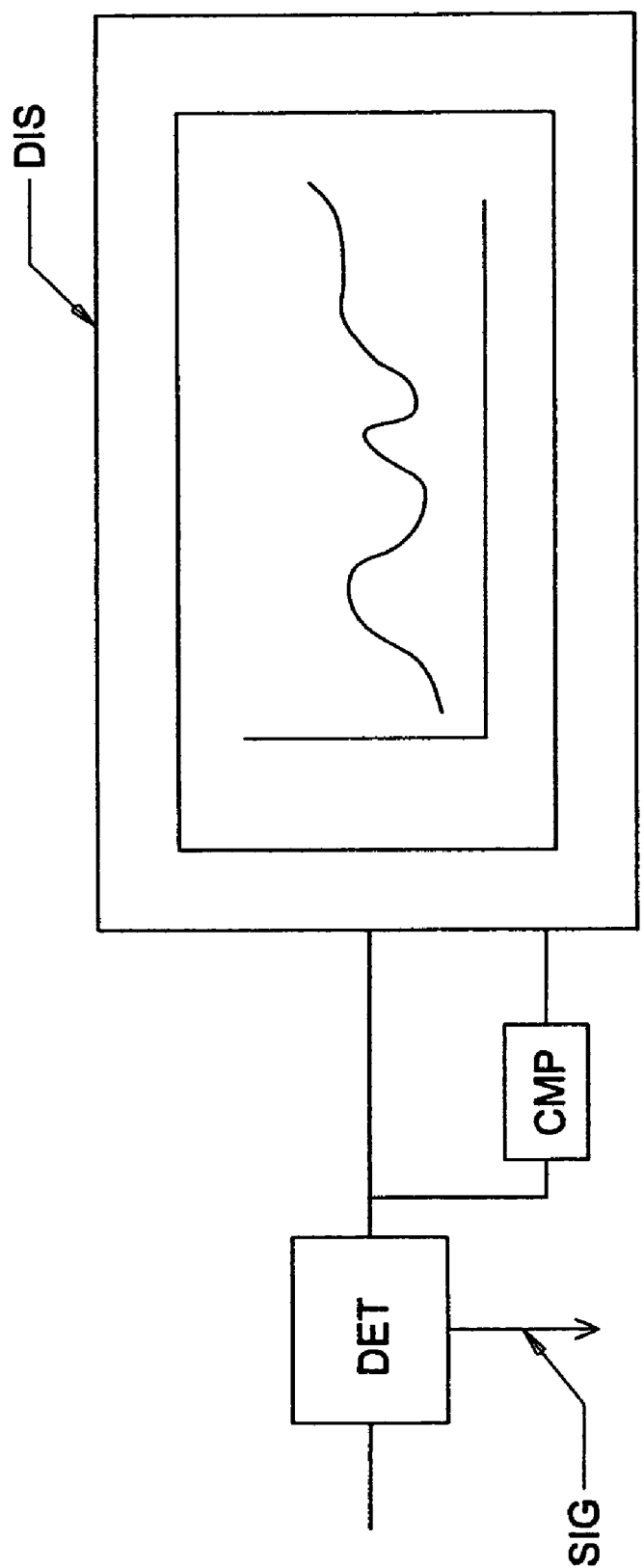
FIG. 3 demonstrates application of data obtained by use of a present invention system.

FIG. 3 demonstrates display (DIS) of at least some data obtained by use of a present invention system or the results of said analysis thereof, which display can be by electronic and/or non-electronic means. Said data can also be applied to provide a signal (SIG) used to cause a concrete and tangible result.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system comprising means for maintaining the location on a sample at which a beam of electromagnetic radiation is caused to impinge, said system comprising:

two mounting arms;

a source for providing a beam of electromagnetic radiation to a small location on a sample;

a sample support positioned between said mounting arms; said mounting arms projecting from said sample support stage at equal but oppositely directed acute angles; and a detector;

said source being mounted to one of said mounting arms and said detector being mounted to the other of said mounting arms such that in use a beam of electromagnetic radiation from said source is directed to interact with a sample placed on the support therefore, and reflect into said detector;

said system further comprising at least one motor driven component which comprises a motor;

said at least one motor driven component being mounted to one or the other of said mounting arms and positioned such that in use the beam of electromagnetic radiation from said source, which beam is directed to interact with a sample placed on the support therefore and reflect into said detector, interacts with said motor driven component;

said system being distinguished by the presence of a securing means for damping vibrations caused by the operation of said motor, said securing means comprising a stationary support which is separate from, and in addition to said two mounting arms, to which separate support said motor is also attached, with the result being that vibrations caused by operation of said motor are damped and therefore cause less change in the locus of said beam of electromagnetic radiation as it progresses from the source to the detector, than result when said motor driven component is not so attached to said stationary support.

2. A system as in claim 1, in which the beam of electromagnetic radiation is polarized and the motor driven component comprises means for altering said polarization of said beam of electromagnetic radiation which interacts therewith.

3. A system as in claim 1 in which said means for damping vibrations caused by the operation of said motor comprise a securing means which rigidly secures said motor to said stationary support.

4. A system as in claim 1 in which said means for damping vibrations caused by the operation of said motor comprise said motor being secured to said stationary support via vibration absorbing damping means.

5. A system as in claim 1 in which said means for damping vibrations caused by the operation of said motor comprises a stationary support and securing means which secures said motor to said stationary support, are more massive than is necessary to support the motor, said mass serving to dampen vibrations.

6. A method of maintaining the location on a sample at which a beam of electromagnetic radiation impinges, comprising the steps of:
   a) providing a system comprising means for maintaining the location on a sample at which a beam of electromagnetic radiation is caused to impinge, said system comprising:
      two mounting arms;
      a source for providing a beam of electromagnetic radiation to a small location on a sample;
      a sample support positioned between said mounting arms;
      said mounting arms projecting from said sample support stage at equal but oppositely directed acute angles; and a detector;
      said source being mounted to one of said mounting arms and said detector being mounted to the other of said mounting arms such that in use a beam of electromagnetic radiation from said source is directed to interact with a sample placed on the support therefore, and reflect into said detector;
      said system further comprising at least one motor driven component which comprises a motor;
      said at least one motor driven component being mounted to one or the other of said mounting arms and positioned such that in use the beam of electromagnetic radiation from said source, which beam is directed to interact with a sample placed on the support therefore and reflect into said detector, interacts with said motor driven component;
      said system being distinguished by the presence of a securing means for damping vibrations caused by the operation of said motor, said securing means comprising a stationary support which is separate from, and in addition to said two mounting arms, to which separate support said motor is also attached, with the result being that vibrations caused by operation of said motor are damped and therefore cause less change in the locus of said beam of electromagnetic radiation as it progresses from the source to the detector, than result when said motor driven component is not so attached to said stationary support;
   b) in functional combination with step a causing said means for damping vibrations caused by the operation of said motor to be functionally attached to said motor;
   c) causing an electromagnetic beam from the source to pass through said motor driven component and impinge on said sample while said motor is caused to operate, and detecting electromagnetic radiation emerging from said sample with a data detector;

to the end that vibrations produced by the operation of said motor cause less change in the locus of said beam than would be the case if said means for damping vibrations caused by the operation of said motor were not attached thereto;

said method being further characterized by at least one selection from the group consisting of:
   storing at least some data provided by said data detector in machine readable media;
      analyzing at least some of the data provided by said data detector and storing at least some of the results of said analysis in machine readable media;
      displaying at least some data provided by said data detector by electronic and/or non-electronic means;
      analyzing at least some of the data provided by said data detector and displaying at least some of the results of said analysis by electronic and/or non-electronic means;
   causing at least some data provided by said data detector to produce a signal which is applied to provide a concrete and tangible result;
   analyzing at least some of the data provided by said data detector and causing at least some thereof to produce a signal which is applied to provide a concrete and tangible result.

* * * * *